United States Patent [19]

Kim

[11] Patent Number: 5,001,235
[45] Date of Patent: Mar. 19, 1991

[54] ANTIBIOTIC BETA-LACTAMS CONTAINING A PYRIDONE CARBOXYLIC ACID OR ACID DERIVATIVE

[75] Inventor: Kyoung S. Kim, Kalamazoo, Mich.

[73] Assignee: The Upjohn Company, Kalamazoo, Mich.

[21] Appl. No.: 438,504

[22] PCT Filed: Feb. 1, 1988

[86] PCT No.: PCT/US88/00206
§ 371 Date: Aug. 24, 1989
§ 102(e) Date: Aug. 24, 1989

[87] PCT Pub. No.: WO88/06587
PCT Pub. Date: Sep. 7, 1988

[51] Int. Cl.$^5$ .................. A61K 31/64; C07D 205/85; C07D 401/14
[52] U.S. Cl. ........................ 540/363; 540/364
[58] Field of Search .................. 540/363, 364

[56] References Cited

U.S. PATENT DOCUMENTS

| 4,587,047 | 5/1986 | Breuer | 260/239 A |
| 4,670,553 | 6/1987 | Breuer et al. | 540/363 |
| 4,743,685 | 3/1988 | Breuer | 540/363 |

FOREIGN PATENT DOCUMENTS

| 905502A | 1/1987 | Belgium . |
| 053815 | 12/1981 | European Pat. Off. . |
| 053816 | 12/1981 | European Pat. Off. . |
| 076758 | 10/1982 | European Pat. Off. . |
| 085291 | 10/1983 | European Pat. Off. . |
| 114128 | 7/1984 | European Pat. Off. . |
| 246786 | 11/1987 | European Pat. Off. . |
| 096297 | 12/1983 | Fed. Rep. of Germany . |
| 2181130A | 4/1987 | United Kingdom . |
| 87/07273 | 12/1987 | World Int. Prop. O. . |

OTHER PUBLICATIONS

Breuer, H. et al., Abstract 371, Sep. 29–Oct. 2, 1985, XXV Interscience Conference on Antimicrobial Agents and Chemotherapy, Minneapolis, Minnesota.
Tanaka, S. K. et al., Abstract 372, Sep. 29–Oct. 2, 1985, XXV Interscience Conference on Antimicrobial Agents and Chemotherapy, Minneapolis, Minnesota.
Clark, J. M. et al., Abstract 373, Sep. 29–Oct. 2, 1985, XXV Interscience Conference on Antimicrobial Agents and Chemotherapy, Minneapolis, Minnesota.
Breuer, H. et al., Abstract 847, Sep. 28–Oct. 1, 1986, XXVI Interscience Conference on Antimicrobial Agents and Chemotherapy, New Orleans, Louisiana.
Whitney, R. R. et al., Abstract 848, Sep. 28–Oct. 1, 1986, XXVI Interscience Conference on Antimicrobial Agents and Chemotherapy, New Orleans, Louisiana.
Pilkiewicz, F. G. and Remsburg, B. J., Abstract 849, Sep. 28–Oct. 1, 1986, XXVI Interscience Conference on Antimicrobial Agents and Chemotherapy, New Orleans, Louisiana.

Primary Examiner—Mark L. Berch
Attorney, Agent, or Firm—Donald L. Corneglio

[57] ABSTRACT

This invention presents novel 2-azetidinone compounds of the formula

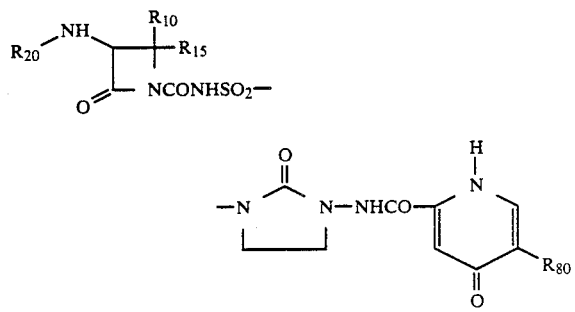

wherein $R_{80}$ is $-CO_2R_5$ or $-CONR_6R_7$; wherein $R_5$ is hydrogen or ($C_1$-$C_4$) alkyl; and wherein $R_6$ and $R_7$ are the same or different and are hydrogen, ($C_1$-$C_4$ alkyl), or —OH with the proviso that when $R_6$ is —OH, $R_7$ is other than —OH. These compounds are useful as antibacterial agents to eradicate or control susceptible microbes. Intermediates and processes for making these compounds are also disclosed.

5 Claims, No Drawings

ANTIBIOTIC BETA-LACTAMS CONTAINING A PYRIDONE CARBOXYLIC ACID OR ACID DERIVATIVE

FIELD OF THE INVENTION

This invention encompasses novel 2-azetidinone compounds which have useful antimicrobial activity.

INFORMATION DISCLOSURE

Derivatives of 2-azetidinone which have antimicrobial and $\beta$-lactamase inhibitory activity are known in the art. European Patent Applications Nos. 0053815, 0053816, 0076758, and 0096297 disclose $\beta$-lactams with various substituents at the $C_4$ position of the ring. European Patent Application No. 0053816 discloses 2-azetidinone compounds substituted at the $C_4$ position with an organic residue.

Abstracts from papers presented by Squibb Institute for Medical Research at the 25th and 26th Interscience Conferences on Antimicrobial Agents and Chemotherapy disclose antibacterial compounds with a substituted-sulfonylaminocarbonyl group at the N-1 position and a 2-(2-amino-4-thiazolyl)-2-(1-carboxy-1-methylethoxy)-iminoacetamido group at the $C_3$ position.

U.S. Pat. No. 4,587,047, filed Apr. 1, 1982, issued May 6, 1986, discloses substituted sulfonylaminocarbonyl-2-azetidinones. U.S. patent application Ser. No. 444,771, filed Nov. 26, 1982 and European Patent Application No. 0085291, filed Mar. 1, 1983, published Oct. 8, 1983, disclose substituted sulfonylaminocarbonyl-2-azetidinones containing a terminal substituted heterocycle in the sulfonylaminocarbonyl activating group. U.K. Patent Application No. 8623151, filed Sept. 26, 1986, and Belgium Patent No. 905502A disclose sulfonylaminocarbonyl-2-azetidinones containing an imidazolidonylaminocarbonyl-1,4-dihydro-5-hydroxy-4-oxo-2-pyridinone in the activating group.

SUMMARY OF THE INVENTION

The present invention teaches novel 2-azetidinone analogs useful as microbial growth inhibitors. This invention includes enantiomers, diastereomeric and racemic mixtures of these compounds. Intermediates and processes for preparing these compounds are also disclosed.

Novel 2-azetidinone analogs within the scope of this invention are represented by Formula I and pharmacologically acceptable salts thereof; wherein $R_{10}$ and $R_{15}$ are the same or different and are hydrogen, $(C_1-C_8)$ alkyl, $(C_2-C_8)$ alkenyl, $(C_2-C_8)$ alkynyl, $(C_3-C_8)$ cycloalkyl, phenyl optionally substituted with between 1 and 3 substituents selected from the group consisting of halogen, nitro, $(C_1-C_4)$-alkyl, and $(C_1-C_4)$alkoxy, benzyl optionally substituted with between 1 and 3 substituents selected from the group consisting of halogen, nitro, $(C_1-C_4)$alkyl, and $(C_1-C_4)$alkoxy, —CH$_2$OCOCH$_2$NHR$_4$, —CH$_2$OCO$_2$R$_{30}$, —CH$_2$F, or —CHF$_2$; wherein $R_4$ is hydrogen, —COH or —CO—O—C(CH$_3$)$_3$; wherein $R_{30}$ is $(C_1-C_8)$alkyl, —(CH$_2$)$_2$NH$_2$, —(CH$_2$)$_2$NH(CH$_3$), —(CH$_2$)$_2$NH—CO—O—C(CH$_3$)$_3$, —(CH$_2$)$_2$N(CH$_3$)—CO—O—C(CH$_3$)$_3$, —(CH$_2$)$_2$OC(O)NH$_2$, —(CH$_2$)$_2$Cl, —(CH$_2$)$_2$OCH$_3$ or —(CH$_2$)$_2$NHCOH; wherein $R_{20}$ is an acyl group derived from a carboxylic acid; wherein $R_{80}$ is —CO$_2$R$_5$ or —CONR$_6$R$_7$; wherein $R_5$ is hydrogen or $(C_1-C_4)$ alkyl; and wherein $R_6$ and $R_7$ are the same or different and are hydrogen, $(C_1-C_4)$ alkyl, or —OH with the proviso that when $R_6$ is OH, $R_7$ is other than —OH.

Novel compounds within the scope of this invention which are useful as intermediates to 2-azetidinone analogs having microbial growth inhibition include compounds of Formula I wherein $R_4$ is —COH and —CO—O—C(CH$_3$)$_3$; and wherein $R_{30}$ is —(CH$_2$)$_2$NH—CO—O—(CH$_3$)$_3$ and —(CH$_2$)$_2$N(CH$_3$)—CO—O—(CH$_3$)$_3$.

A detailed description of the acyl groups included in $R_{20}$ is found in U.S. Pat. No. 4,478,749, column 8, line 41 to column 12, line 50, as those terms are defined at column 7, line 34 through column 8, line 22, all of which is incorporated by reference herein.

Preferred acyl groups of $R_{20}$ include those which have been used to acylate 6-aminopenicillanic acid, 7-aminocephalosporic acid and their derivatives which can be found in "Chemistry and Biology of $\beta$-Lactam Antibiotics, Vol. 1, R. B. Morin and M. Gorham, ed., Academic Press, N.Y. (1982) and include the following list: 2-Cyanoacetyl, Aminophenylacetyl, Amino(4-hydroxyphenyl)acetyl, $\alpha$(Thien-2-yl)acetyl, $\alpha$(Thien-3-yl)acetyl, Phenylacetyl, Hydroxyphenylacetyl, (Formyloxy)phenylacetyl, [(Trifluoromethyl)thio]acetyl, 2-(3,5-Dichloro4-oxo-1(4H)-pyridyl)acetyl, (1H-Tetrazol-1-yl)acetyl, (2-Amino-4-thiazolyl)-2-methoxyiminoacetyl, 2-[(Cyanomethyl)thio]acetyl, [[(4Ethyl-2,3-dioxo-1-piperizinyl)carbonyl]amino]phenylacetyl, [[(4-Ethyl-2,3-dioxo-piperazinyl)carbonyl]amino](4-hydroxyphenyl)-acetyl, 2-(Aminomethyl)phenylacetyl, 4-(Carbamoylcarboxymethylene)-1,3-dithiethane-2-carbonyl, 3-(o-Chlorophenyl)-5-methyl-4-isoxazole-carbonyl, 2-p-[(1,4,5,6-Tetrahydro-2-pyrimidinyl)phenyl]acetyl, Amino-1,4-cyclohexadien-1-yl-acetyl, Phenylsulfoacetyl, (2R)-2-amino-2-(m-methanesulfonamidophenyl)acetyl, (2-Amino-4-thiazolyl)-2-(1-carboxyl-1-methylethoxy)iminoacetyl, 2-(1H-Tetrazol-1-yl)acetyl, (2,3-Dihydro-2-imino-4-thiazolyl)(methoxyimino)acetyl, (2-Amino-4-thiazol)carboxymethoxyiminoacetyl, (2-Aminopyridin-6-yl)methoxyiminoacetyl, (2-Aminopyridin-6-yl)carboxymethoxyiminoacetyl, (4-Amino-2-pyrimidyl)methoxyiminoacetyl, (5-Amino-1,2,4-thiadiazol-3-yl)-2-methoxyiminoacetyl, (5-Amino-1,2,4-thiadiazol-3-yl)-2-carboxymethoxyiminoacetyl, (5-Amino-1,2,4-thiadiazol-3-yl)-1-carboxy-1-methylethoxy)-iminoacetyl,D-$\alpha$[[(Imidazolidin-2-on-1-yl)-carbonyl]amino]phenylacetyl, D-$\alpha$[[(3-mesyl-imidazolidin-2-on-1-yl)carbonyl]amino]phenylacetyl, 2,6-Dimethylbenzoyl, (S)-2-(4-hydroxy-1,5-naphthyridine-3-carboxamido-2-phenylacetyl.

Preferred compounds within the scope of this invention include compounds wherein the organic acid derivative, $R_{20}$, is an oximinoacyl moiety represented by Formula II; wherein $R_{40}$ is —CH$_3$, —CH$_2$CO$_2$R$_{41}$, or —C(CH$_3$)$_2$CO$_2$R$_{41}$, wherein $R_{41}$ is hydrogen, $(C_1-C_4)$ alkyl, —CH(C$_6$H$_5$)$_2$,—CH$_2$(C$_6$H$_5$), or a cation; wherein $R_{50}$ is hydrogen, —CO—O—C(CH$_3$)$_3$, —CO—O—CH$_2$—(C$_6$H$_5$), or —C(C$_6$H$_5$)$_3$.

Novel compounds within the scope of this invention containing an oximinoacyl moiety represented by Formula II which are useful as intermediates to 2-azetidinone analogs having microbial growth inhibition include compounds wherein $R_{41}$ is $(C_1-C_4)$ alkyl, —CH—(C$_6$H$_5$)$_2$, or —CH$_2$(C$_6$H$_5$); and wherein $R_{50}$ is —CO—O—C(CH$_3$)$_3$, —CO—O—CH$_2$—(C$_6$H$_5$), or —C(C$_6$H$_5$)$_3$.

The compounds of this invention are identified in two ways: by descriptive name and by numerical identification which corresponds to the appropriate structure contained in the structure chart. In appropriate situations, the proper stereochemistry is represented in the structure charts as well.

The various carbon moieties are defined as follows: Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl, n-octyl, isooctyl, n-nonyl, n-decyl, n-undecyl, and n-dodecyl; Alkoxy refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, and t-butoxy; Alkenyl refers to a radical of an aliphatic unsaturated hydrocarbons having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, 2-pentenyl, 3-pentenyl, 4-pentenyl, 1-methyl-4-pentenyl, 3-methyl-1-pentenyl, 3-methyl-2-pentenyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl; Alkynyl refers to a radical of an aliphatic unsaturated hydrocarbons having a triple bond and includes both branched and unbranched forms such as ethynyl, 1-methyl-1-ethynyl, 1-propynyl, 2-propynyl, 1-butynyl, 2-butynyl, 3-butynyl, 2-methyl-1-butynyl, 1-pentynyl, 2-pentynyl, 3-pentynyl, 4-pentynyl, 1-methyl-4-pentynyl, 3-methyl-1-pentynyl, 3-methyl-2-pentynyl, 1-hexynyl, 2-hexynyl, 3-hexynyl, 4-hexynyl, 1-methyl-4-hexynyl, 3-methyl-1-hexynyl, 3-methyl-2-hexynyl, 1-heptynyl, 2-heptynyl, 3-heptynyl, 4-heptynyl, 1-methyl-4-heptynyl, 3-methyl-1-heptynyl, 3-methyl-2-heptynyl, 1-octynyl, 2-octynyl, or 3-octynyl.

Cycloalkyl refers to a radical of a saturated cyclic hydrocarbon such as cyclopropyl, cyclobutyl, cyclopentyl, cyclohexyl, cycloheptyl, cyclooctyl or adamantyl.

Halogen refers to a radical of fluorine, chlorine, bromine, or iodine.

Unless otherwise indicated, in the above description and throughout this document, the parenthetical term $(C_n-C_m)$ is inclusive such that a compound of $(C_1-C_4)$ would include compounds of 1, 2, 3 and 4 carbons and their isomeric forms.

It will be apparent to those skilled in the art that compounds of this invention may exist in different tautomeric forms. The scope of this invention includes all tautomeric forms in addition to those represented in the formulas used herein.

It will be apparent to those skilled in the art that compounds of this invention may contain several chiral centers. The scope of this invention includes all enantiomeric or diastereomeric forms of Formula I compounds either in pure form or as mixtures of enantiomers or diastereomers. Specifically, the compounds of this invention have chiral carbon atoms at positions $C_3$ and $C_4$ of the β-lactam ring. The preferred form is cis at centers 3 and 4 and the preferred stereochemistry at $C_3$ and $C_4$ is 3(S) and 4(S). The phrase "cis at centers 3 and 4" means that the substituents at C-3 and C-4 are both oriented on the same side of the β-lactam ring.

The scope of this invention includes the pharmacologically acceptable acid salts of the disclosed compounds. Acid salts are formed by reacting the compounds described herein with the appropriate acid in a suitable solvent. Suitable acids for this purpose include hydrochloric, sulfuric, phosphoric, hydrobromic, hydroiodic, acetic, lactic, citric, succinic, benzoic, salicylic, palmoic, cyclohexansulfamic, methanesulfonic, naphthalenesulfonic, p-toluenesulfonic, maleic, fumaric, or oxalic.

The scope of this invention includes the pharmacologically acceptable salts of the disclosed compounds. Such salts include the following cations but are not limited to these: alkali metal ions such as potassium, sodium, lithium, alkaline earth metal ions such as magnesium or calcium and ammonium ions such as ammonium, tetralkylammonium and pyridinium. Metal salts are formed by suspending the compounds in water or other suitable solvent and adding a dilute metal base such as sodium or potassium bicarbonate until the pH is between 6 and 7.

The compounds of this invention and their respective pharmacologically acceptable salts have antibiotic activity against a variety of gram-negative bacteria including Escherichia coli, Klebsiella pneumoniae, and Pseudomonas aeruginosa. The compounds are useful for treating bacterial infections in animals, including and most preferably humans. Compounds of the invention are tested for in vitro antimicrobial activity using standard testing procedures such as the determination of minimum inhibitory concentration (MIC) by agar dilution as described in "Methods for Dilution Antimicrobial Susceptibility Tests for Bacteria That Grow Aerobically" (M7-A) Published December 1985 by the National Committee for Clinical Laboratory Standards, 771 East Lancaster Avenue, Villanova, Pa. 19084. Briefly, MIC values are determined in unsupplemented Mueller Hinton Agar (MHA). The compounds tested are diluted serially into molten MHA at 47° C. The agar is poured into petri dishes and allowed to harden. The various bacteria used for testing are grown overnight on MHA at 35° C. and transferred to Tryptiease Soy Broth (TSB) until a turbidity of 0.5 McFarland standard is obtained. The bacteria are diluted one to 20 in TSB and inoculated on the plates (1 μl using a Steers replicator). The plates are incubated at 35° C. for 20 hours and the MIC is read to be the lowest concentration of drug that completely inhibits visible growth of the bacterium. The MIC test results of two typical compounds of this invention, Compound 14 which is (3S)-3-[2-(2-Amino-4-thiazolyl)-Z-(2)-carboxyisopropyloxyimino)acetamido]-1-[(3-carboxy-4-pyridon-6-yl)carbonylamino-1-(2-imidazolidone-3-yl)sulfonylaminocarbonyl]-2-azetidinone trisodium salt and Compound 17 which is (3S)-3-[2-(2-Amino-4-thiazolyl)-Z-(2)-(carboxyisopropyloxyamino)acetamido]-1-[(3-hydroxyaminocarbonyl-4-pyridon-6-yl)carbonylamino-1-(2-imidazolidone-3-yl)sulfonylaminocarbonyl]-2-azetidinone, are given in Table I.

Various compositions of the present invention are presented for administration to humans and animals in unit dosage forms, such as tablets, capsules, pills, powders, granules, sterile parenteral solutions or suspensions, eye drops, solutions or suspensions, and emulsions containing suitable quantities of compounds of Formula I.

For oral administration solid or fluid unit dosage forms can be prepared. For preparing solid compositions, the compounds of this invention are mixed with conventional ingredients such as talc, magnesium stearate, dicalcium phosphate, magnesium aluminum silicate, calcium sulfate, starch, lactose, acacia, methylcellulose, and/or functionally similar pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

For preparing fluid compositions, the compounds of this invention are dissolved in an aqueous vehicle together with sugar, aromatic flavoring agents and preservatives to form a syrup. An elixir is prepared by using a hydroalcoholic vehicle such as ethanol, suitable sweeteners such as sugar and saccharin, and aromatic flavoring agents. Suspensions are prepared in an aqueous vehicle with the aid of a suspending agent such as acacia, tragacanth, or methylcellulose.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compounds of Formula I may also be administered in a carrier suitable for topical administration, such carriers include creams, ointments, lotions, pastes, jellies, sprays, aerosols, bath oils, or other pharmaceutical carriers which accomplish direct contact between the compound and the surface of the skin area to be treated. In general pharmaceutical preparations may comprise from about 0.01% to about 10%, and preferably from about 0.1% to about 5% by w/w of the active compound in the suitable carrier.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 g.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on the unique characteristics of the active material and the particular effect to be achieved and the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, drops, ampules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans having an average weight of 70 kg is from about 50 to about 3000 mg of compound in a single dose. More specifically, the single dose is from about 100 mg to 2000 mg of compound. Typically the dosages are given one to 4 times per day.

The process for making compounds of Formula I is illustrated in Charts A and B. The requirements for protecting groups in the processes of Charts A and B are well recognized by one skilled in the art of organic chemical synthesis and suitable protecting groups are used in the processes of Charts A and B. It is recognized that conditions for introduction and removal of protecting groups should not detrimentally alter any other groups in the molecule.

Examples of suitable nitrogen protecting groups are: benzyl; triphenylmethyl (trityl); trialkylsilyl, such as trimethylsilyl or t-butyldimethylsilyl; t-butoxycarbonyl (t-BOC or BOC); benzyloxycarbonyl (Cbz); trifluoroalkanoyl, such as trifluoroacetyl or trifluoropropionyl; or diphenyl(methyl)silyl. Introduction and removal of such nitrogen protecting groups are well known in the art of organic chemistry: See, for example, (1) J. F. W. McOmie, Advances in Organic Chemistry, 3:191–281 (1963); (2) R. A. Boissonas, Advances in Organic Chemistry, 3:159–190 (1963); (3) "Protective Groups in Organic Chemistry", J. F. W. McOmie, Ed., Plenum Press, New York, page 74 (1973), and (4) "Protective Groups in Organic Synthesis", Theodora W. Greene, John Wiley and Sons, New York (1981).

Under certain circumstances it may be necessary to protect two or more nitrogen atoms with different protecting groups allowing selective removal of one protecting group while leaving the remaining protecting groups in place. For example, the Cbz group can be selectively removed in the presence of the BOC group and vice versa.

The compounds of this invention are prepared by the procedures outlined in Charts A and B. The substituents at the $C_4$ position defined by $R_{10}$ and $R_{15}$ are prepared by procedures outlined in Chart A. The starting compound cis-(±)-4-(methoxycarbonyl)-3-[[(benzyloxy)-carbonyl]amino]-2-azetidinone, A—1, is known. J. Org. Chem., 2765–2767 (1982). The trans compound is known or is made by known methods. Thus compound A—1 is either cis or trans with respect to the substituents on $C_3$ and $C_4$. It is recognized that alternative protecting groups could be used in place of the benzyloxycarbonyl group of compound A—1. See also, W. F. Huffman et al., J. Am. Chem. Soc., 2352 (1977); D. B. Bryan et al., J. Am. Chem. Soc., 2353 (1977).

The $C_4$-carbomethoxy group of compound, A—1, is reduced to the $C_4$-hydroxymethyl group of compound, A—2, by use of metal hydride reducing reagents, such as sodium borohydride or zinc borohydride, in ether solvents, such as diethyl ether or tetrahydrofuran, at a temperature range of 0° to 80° C. The product is obtained after a normal aqueous work-up procedure followed by column chromatography on silica gel.

The hydroxymethyl group of compound, A—2, reacts with $HO_2CCH_2$—$NHR_4$ wherein $R_4$ is —COH or —BOC to produce compound A—4 using approximately equimolar quantities of the acid, 1-hydroxy-1-benzotriazole (HOBT), and a carbodiimide, such as dicyclohexylcarbodiimide (DCC) and a catalytic amount of 4-dimethylaminopyridine. The choice of solvents is methylene chloride, dimethylformamide or a combination of both solvents and the reaction is carried out in general at the temperature range of 0° C. to ambient temperature. The desired compound is obtained after filtration of precipitated dicyclohexylurea and removal of HOBT by washing with aqueous sodium bicarbonate solution and then column chromatography on silica gel.

To prepare compounds represented by A—3, the hydroxymethyl compound, A—2, reacts with a suitable protected chloroformate ester of formula $ClCO_2R_{30}$ where $R_{30}$ is $(C_1-C_8)$alkyl, —$(CH_2)_2NH$—CO—O—$(CH_3)_3$, —$(CH_2)_2N(CH_3)$—CO—O—$(CH_3)_3$, —$(CH_2)_2OC(O)NH_2$, —$(CH_2)_2Cl$, —$(CH_2)_2OCH_3$ or —$(CH_2)_2NHCOH$, to give the compound, A—3. The reaction conditions involve the use of an inert solvent such as methylene chloride, tetrahydrofuran, or dimethylformamide at −20° C. to 30° C. in the presence of a slight excess of organic base, such as pyridine, 2,4-lutidine, or triethylamine. Following extractive workups involving successive washes with acid and base, the products are isolated by chromatography or crystallization. Some chloroformate esters are commercially available and others are be prepared according to the teaching of Huntress, "Organic Chlorine Compounds," John Wiley and Sons, Inc., New York, N.Y. (1948); F. Stain et al., J. Am. Chem. Soc., 72:1254 (1950), H. G. Ashburm et al., J. Am. Chem. Soc., 60:2933 (1938). Briefly, the process described in these references is to contact an alcohol with an excess of phosgene either neat or in an organic solvent. After workup, the product is usually isolated by vacuum distillation.

An alternative process to prepare compounds represented by A—3, can be used when the desired chloroformate is unavailable. Compound A—2 is placed in a solvent such as methylene chloride, ethyl acetate, tetrahydrofuran, or acetonitrile containing a slight excess of an organic base, such as pyridine, triethylamine, or 2,4-lutidine, and is reacted at −20° C. to 30° C. with a solution of phosgene in an inert solvent, such as toluene, benzene or methylene chloride. The intermediate chloroformate thus formed is not isolated, but is treated with a molar equivalent of the suitably protected desired alcohol, $R_{30}OH$, where $R_{30}$ is $(C_1-C_8)$alkyl, —$(CH_2)_2NH$—CO—O—$(CH_3)_3$, —$(CH_2)_2$—N(CH$_3$)—CO—O—$(CH_3)_3$, —$(CH_2)_2OC(O)NH_2$, —$(CH_2)_2Cl$, —$(CH_2)_2OCH_3$ or —$(CH_2)_2NHCOH$, in the presence of an organic base in an inert solvent at −20° C. to 30° C. to yield the compound, A—3. This alternative or reversed process is known in the field of steroid chemistry, G. Schubert et al., Die Pharmazie, 35:453 (1980).

To prepare compounds of this invention wherein $R_{10}$ or $R_{15}$ are alkyl, alkenyl, alkynyl, cycloalkyl, substituted phenyl, substituted benzyl or fluoroalkyl, the hydroxyl substituent in compound A—2 is converted to an appropriate leaving group, Lg, by methods known in the art to give compound, A—5. The leaving group is displaced by known nucleophiles by methods known in the art to give compound A—6 wherein R' is alkyl, alkenyl, alkynyl, cycloalkyl, substituted phenyl, substituted benzyl or fluoroalkyl.

To prepare compounds of this invention wherein $R_{10}$ or $R_{15}$ are the same, a suitable amino acid derivative, A—7, is cyclized by known methods to give the substituted four membered ring, A—8, Slusarchyk, W. A., et al., Tetrahedron Letters, 2789–2792 (1986). Deprotection of the lactam nitrogen gives the hydroxy amide, A—9, which is reduced to the $\beta$-lactam by titanium trichloride in tetrahydrofuran and water, Miller, M. J., et al., J. Org. Chem., 1126 (1985), Miller, M. J., et al., J. Org. Chem., 410 (1980), Miller, M. J., et al., Tetrahedron, 2571 (1983). Other procedures to prepare substituted azetidinones are known in the art; see, for example, Teutsch, G., et al., Tetrahedron, 2677–2684 (1986), Teutsch, G., et al., Tetrahedron Letters, 1561–1562 (1984), and U.S. Pat. No. 4,478,749, column 19, lines 1–40.

Optically active compounds of the Formula I of this invention are prepared by the use of the appropriate optically active form of compound, A—1, which is prepared by known methods, Takeda European patent application No. 8310461-3. The resolving agents are any of the known resolving agents such as optically active camphorsulfonic acid, bis-o-toluoyltartaric acid, tartaric acid, and diacetyl tartaric acid which are commercially available and which are commonly used for resolution of amines. See Organic Synthesis, Coll., V: 932 (1978), which describes the resolution of R-(+) and S-(−)-$\beta$-phenylethylamine with (−)-tartaric acid.

The preferred starting compound for making optically active compounds of Formula I, cis-(±)-1-[(2',4'-dimethoxyphenyl)methyl]-4-(methoxycarbonyl)-3-phenylmethoxycarboxyamino-2-azetidinone, is known, Chem. Pharm. Bull., 2646–2659 (1984). The $C_3$ protecting group is removed by hydrogenolysis to produce the corresponding free amine. An appropriate substituted tartaric acid enantiomer is then added such as (+)-di-p-toluoyl-D-tartaric acid and reaction conditions altered to facilitate precipitation of the appropriate azetidinone diastereomeric salt. The tartaric acid is removed by treating the compound with inorganic base such as aqueous sodium bicarbonate to produce the desired resolved amino-azetidinone.

The acidic pyridone is prepared from the known compound, 4-hydroxy-6-methyl-2-pyrone, A—11, by forming the enamine, A—12, with N,N-dimethylformamide in a suitable solvent such as dioxane. The enamine rearranges to the pyridinone, A—13, upon heating in 2-methoxyethanol in the presence of ammonia. The carboxylic acid moiety in compound A—13 is transformed to compounds containing moieties defined by $R_{80}$, compound A—14, by methods known in the art. The methyl group in compound A—14 is oxidized to the acid with selenium dioxide in refluxing dioxane to give compound A—15. The carboxylic acid moiety obtained from the oxidation reaction reacts with aminoimidazolidinone in the presence of dimethylaminopyridine, dicyclohexylcarbodiimide and 1-hydroxybenzotriazole in DMF to give the compound, A—16, which is attached to the β-lactam.

Alternative procedures to complete the rest of the molecule are outlined in Chart B. As shown in Chart B, the benzyloxycarbonyl group of compound, B—1, is removed by catalytic hydrogenolysis using palladium metal supported on carbon or palladium metal itself under a hydrogen gas atmosphere in suitable solvents, such as alcoholic solvents, ether solvents or ethyl acetate, at ambient temperature. The compound, B—2, is obtained by removal of the solid catalyst and removal of the solvent under reduced pressure.

The $C_3$-amino group of compound, B—2, is acylated with a suitable carboxylic acid to produce compound, B—3. This conversion may be carried out by any of a number of amide or peptide forming reaction sequences such as methods described in Methoden der Organischem Chemie, Vierte Auflage, Band XV/2, E. Wunch ed., Georg Thieme Verlag, Stuttgart, p. 1. A preferred acylation process is the use of approximately equimolar quantities of a desired acid, HOBT, and a carbodiimide, such as DCC. The choice of solvents is methylene chloride, dimethylformamide or a combination of both solvents and the reaction is carried out in general at the temperature range of 0° C. to ambient temperature. The desired compound is obtained after filtration of precipitated dicyclohexylurea, removal of HOBT by washing with aqueous sodium bicarbonate solution and column chromatography on silica gel if necessary. Also, the compounds can be made by other methods known in the art, see, for example, J. Am. Chem. Soc., 2401-2404 (1973).

The amide, B—3, reacts with approximately 1.2 to 1.6 equivalents of chlorosulfonyl isocyanate at −20° to 0° C. in organic solvents, such as methylene chloride, acetonitrile or a combination of both solvents to produce the activated azetidinone B—4 which is coupled to a silylated aminoimidazolidinone prepared by reacting N-methyl-N-(trimethylsilyl)-trifluoroacetamide or bis-(trimethylsilyl)-trifluoroacetamide with aminoimidazolidinone, A—16, in organic solvents, such as acetonitrile, methylene chloride or tetrahydrofuran, at ambient temperature. The silylated aminoimidazolidinone reacts with compound B—4 in the presence of a tertiary amine base such as 2,6-lutidine at about 0° C., and the mixture is slowly warmed to room temperature over a period of one to 5 hours. The crude product is obtained after a normal aqueous work-up procedure and followed by purification by appropriate methods, such as column chromatography, known to those skilled in the art. Removal of any remaining protecting groups by known methods gives the N-1-sulfonyl-aminocarbonyl compound, B—5.

Alternatively, following the procedure outlined in Chart B, a methylene chloride solution of the B—1 and 2,6-lutidine reacts with chlorosulfonyl isocyanate at 0° to give B—6. B—6 reacts with an acetonitrile solution of N-methyl-N-(trimethylsilyl)-trifluoroacetamide and an aminoimidazolidinone, A—16, at ambient temperature to give B—7. The benzyl group at the $C_3$ amino group is removed by known methods to give compound B—8 and the free amine is couple with a carboxylic acid in the presence of HOBT and DCC at ambient temperatures. Removal of any remaining protecting groups by known methods gives the N-1-sulfonyl-aminocarbonyl compound, B—5.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1 cis-(±)-4-(Hydroxymethyl)-3-[((phenylmethoxy)-carbonyl)amino]-2-azetidinone

To a stirred solution of zinc chloride (23.2 g) in anhydrous tetrahydrofuran (300 ml) at 0° C. is added sodium borohydride (13.8 g) and the mixture is allowed to warm to room temperature and is stirred overnight. To the mixture is added cis-(±)-4-(methoxycarbonyl)-3-[((phenylmethoxy)amino]-2-azetidinone (39.2 g) and the reaction mixture is slowly heated to 65° C. and stirred at that temperature for 2 hours. The reaction mixture is cooled to 0° C. and 6N hydrochloric acid (200 ml) is added dropwise with stirring. The mixture is poured into ethyl acetate (1 l) and the organic layer is taken. The aqueous layer is saturated with sodium chloride and re-extracted with ethyl acetate (200 ml). The combined organic layer is washed with water (200 ml) and with 200 ml of brine twice and dried over anhydrous sodium sulfate. The solvent is concentrated under reduced pressure to afford a yellow oil which is purified by column chromatography on silica gel (ethyl acetate as eluent) to obtain 24.3 g of the title product. Physical characteristics are as follows:
Melting point 98°-100° C.

EXAMPLE 2 cis-(±)-3-[2[(2-t-Butoxycarbonylamino-4-thiazolyl]2-[(1-t-butoxycarbonylmethoxy)imino]]acetamido-4-hydroxymethyl-2-azetidinone To a stirred solution of cis-(±)-4-(Hydroxymethyl)-3-[((phenylmethoxy)-carbonyl)amino]-2-azetidinone (19.5 g) in methanol (150 ml) is added palladium black (7.6 g) slurried in ethanol (25 ml) and the reaction mixture is stirred under 1 atmosphere of hydrogen gas for 24 hours. Toluene (100 ml) is added to the reaction mixture and it is stirred for 15 minutes. The solid material is filtered and the filtrate solution is concentrated under reduced pressure. The residue is dissolved in methylene chloride (200 ml) and dimethylformamide (500 ml) and cooled in the ice bath. To this cooled solution, 2-[(2-t-butoxycarbonylamino)-4-thiazolyl]-[(1-t-butoxycarbonylmethoxy)imino]carboxylic acid (23.8 g) is added followed by dicyclohexylcarbodiimide (12.6 g) and 1-hydroxybenzotriazole (4.2 g). The reaction mixture is stirred for 3 hours at 0° C. The precipitated solid is filtered and the filtrate solution is partitioned between ethyl acetate (2.5 l) and water (1 l). The organic layer is taken and the aqueous layer is washed with 500 ml of ethyl acetate twice. The combined organic layer is washed with aqueous sodium bicarbonate followed by brine and dried over anhydrous sodium sulfate. It is filtered and the filtrate solution is concentrated under reduced pressure and the residual material is chromatographed on silica gel eluting with 1:1:: hexane:ethyl acetate and ethyl acetate to obtain 14.1 g of the title compound. Physical characteristics are as follows:
Melting point 195° C. (decomp.).

EXAMPLE 3 cis-(±)-3-[2[(2-t-Butoxycarbonylamino-4-thiazolyl]2-[(1-t-butoxycarbonylmethoxy)imino]]acetamido-4-N-formyl-glycinoyloxymethyl-2-azetidinone To a mixture of cis-(±)-3-[2[(2-t-Butoxycarbonylamino-4-thiazolyl]2-[(1-t-butoxycarbonylmethoxy)imino]]acetamido-4-hydroxymethyl-2-azetidinone (4.5 g), 1-hydroxybenzotriazole (1.216 g), dimethylaminopyridine (122 mg), N-formylglycine (1.62 g) and in the presence of a small amount of 4A molecular sieves in 60 ml of methylene chloride and 6 ml of dimethylformamide, dicyclohexylcarbodiimide (3.25 g) is added with stirring at room temperature. The reaction is complete in 2 hours. The precipitated solid is filtered off, washed with methylene chloride (50 ml) and the filtrate solution is stirred with aqueous sodium bicarbonate (1.89 g sodium bicarbonate in 40 ml water) at room temperature for 15 minutes. The organic layer is taken, dried over sodium sulfate and concentrated under reduced pressure. The residue is passed through the medium pressure silica gel column eluting with 3:1:: hexane:ethyl acetate and ethyl acetate to obtain 3.6 g of the title compound. Physical characteristics are as follows:
Melting point 108°–110° C.

EXAMPLE 4

Alternative preparation of cis-(±)-4-(Hydroxy-methyl)-3-[((phenylmethoxy)carbonyl)amino]-2-azetidinone A solution of 1.63 g of sodium borohydride in 25 ml of water is added dropwise to a well stirred solution of 3.0 g of cis-(±)-4-(methoxycarbonyl)-3-[((phenylmethoxy)carbonyl)amino]-2-azetidinone in 190 ml of tetrahydrofuran. The addition is made over a period of 10 minutes while stirring in an ice bath. The reaction is stirred for 3 hours. Methylene chloride (250 ml) is added followed by anhydrous sodium sulfate. A clear solution is obtained by filtration. The solvent is removed and the residue is dissolved in acetone. The solution is clarified by filtration and concentrated to give 2.84 g of the title compound. Physical characteristics are as follows:
$^{13}C$ NMR ($\delta$, CH$_3$OH-d$_6$): 55.9, 60.2, 61.6, 67.9, 128.7–129.3, 137.6, 158, 170.7.

EXAMPLE 5 cis-(±)-4-[Methoxycarbonyl)oxymethyl]-3-[((phenylmethoxy)-carbonyl)amino]-2-azetidinone Methyl chloroformate (2.42 g) is added dropwise to a solution of 3.2 g of cis-(±)-4-(Hydroxy-methyl)-3-[((phenylmethoxy)carbonyl)-amino]-2-azetidinone and 3.03 g of pyridine in 100 ml of methylene chloride while stirring at 0° C. After one hour an additional 0.5 g of methyl chloroformate is added. The reaction mixture is stirred an additional 0.5 hour and then washed successively with dilute mineral acid (e.g., HCl or H$_2$SO$_4$), water and potassium bicarbonate solution. Evaporation of the solvent and trituration of the residue with ethyl acetate affords 2.48 g of the title compound. Physical characteristics are as follows:
Melting point 155°–158° C.

According to the procedures of Example 5, the following compounds are also prepared:
cis-(±)-4-[(Formylaminoethoxycarbonyl)oxymethyl]-3-[((phenylmethoxy)carbonyl)amino]-2-azetidinone;

cis-(±)-4-[(t-Butoxycarbonylaminoethoxycarbonyl)oxymethyl]-3-[((phenylmethoxy)carbonyl)amino]-2-azetidinone;

cis-(±)-4-[(Aminocarbonyloxyethoxycarbonyl)oxymethyl]-3-[((phenylmethoxy)carbonyl)amino]-2-azetidinone; and cis-(±)-4-[(Chloroethoxycarbonyl)oxymethyl]-3-[((phenylmethoxy)-carbonyl)amino]-2-azetidinone.

EXAMPLE 6 cis-(±)-1-[(Chlorosulfonyl)aminocarbonyl]-4-[(methoxycarbonyl)oxymethyl]-3-[((phenylmethoxy)carbonyl)-amino]-2-azetidinone Chlorosulfonyl isocyanate (175 mg) is added dropwise to a suspension of 382 mg of cis-(±)-4-[Methoxycarbonyl)oxymethyl]-3-[((phenylmethoxy)-carbonyl)amino]-2-azetidinone in 8 ml of methylene chloride while stirring in an ice bath. The bath is removed after 20 minutes and the mixture stirred at ambient conditions. Evaporation of the solvent under vacuum leaves the title compound as a glass which is used without purification.

According to the procedure of Example 6, the following chlorosulfonyl compounds are also prepared:
cis-(±)-1-[(Chlorosulfonyl)aminocarbonyl]-4-[(formylaminoethoxycarbonyl)-oxymethyl]-3-[((phenylmethoxy)carbonyl)amino]-2-azetidinone;

cis-(±)-1-[(Chlorosulfonyl)aminocarbonyl[-4-[(t-butoxycarbonylaminoethoxycarbonyl)-oxymethyl]-3-[((phenylmethoxy)carbonyl)amino]-2-azetidinone;

cis-(±)-1-[(Chlorosulfonyl)aminocarbonyl]-4-[(aminocarbonyloxyethoxycarbonyl)-oxymethyl]-3-[((phenylmethoxy)carbonyl)amino]-2-azetidinone; and cis-(±)-1-[(Chlorosulfonyl)aminocarbonyl]-4-[(chloroethoxycarbonyl)oxymethyl]-3-[((phenylmethoxy)-carbonyl)amino]-2-azetidinone.

EXAMPLE 7

3-(Dimethylaminomethylene)-4-oxo-6-methyl-2-pyrone

N,N-dimethylformamide dimethyl acetal (150 ml) is added dropwise to a mixture of 4-hydroxy-6-methyl-2-pyrone (100 g) in dioxane (400 ml) at 0° C. over 20 minutes. The mixture is warmed to room temperature and stirred an additional 4 hours. The precipitated solid is filtered, washed with isopropanol and dried to give 85.0 g of the title compound. The filtrate is concentrated and isopropanol (300 ml) is added to the residue. This mixture is kept at 0° C. overnight to give an additional 18.8 g of the title compound. Physical characteristics are as follows:
Melting point 152°–153° C.

EXAMPLE 8

6-Methyl-4-(1H)-pyridone-3-carboxylic acid

A mixture of 3-(dimethylaminomethylene)-4-oxo-6-methyl-2-pyrone (85.0 g) and ammonium hydroxide (500 ml) is slowly heated to 70° C. with the condenser outlet open. The mixture is heated at 70°-80° C. for 3 hours, concentrated to a volume of about 100 ml and acidified with 3N HCl to pH 5. The product is filtered and washed with water and diethyl ether to give 38.6 g of the title compound. Physical characteristics are as follows:

Melting point 266°-268° C. (dec.).

EXAMPLE 9

6-Methyl-4-(1H)-pyridone-3-carboxylic acid benzyl ester

A mixture of 6-methyl-4-(1H)-pyridone-3-carboxylic acid (16.0 g) and carbonyldiimdazole (23.0 g) in DMF (150 ml) is heated at 55°-60° C. for 2 hours. The mixture is cooled to room temperature, filtered and washed with THF (50 ml) to give 20.5 g of intermediate product. The intermediate product is mixed with benzyl alcohol (20 ml) in DMF (100 ml) and cooled to 0° C. Sodium hydride (5.4 g of 50% NaH dispersed in oil) is added to the cooled mixture and the mixture is slowly warmed to room temperature. After 30 minutes at room temperature, acetic acid (0.5 ml) is added and the solvent is removed. The residue is partitioned between methylene chloride (500 ml) and water (100 ml), the organic layer is dried over sodium sulfate and concentrated. Trituration of the residue with diethyl ether gives 19.0 g of the title compound. Physical characteristics are as follows:

IR (KBr) 1728, 1648 cm$^{-1}$.

EXAMPLE 10

4-Oxymethoxymethyl-6-methyl-3-carboxylic acid pyridine benzyl ester

Sodium hydride (2.3 g of 50% NaH dispersed in oil) is added in several portions to a slurry of 6-methyl-4-(1H)-pyridone-3-carboxylic acid benzyl ester (10.0 g) in DMF (70 ml) at 0° C. After 5 minutes, chloromethyl methyl ether (3.42 ml) is added to the mixture. After one hour the solvent is removed and the residue is partitioned between methylene chloride (200 ml) and water (50 ml). The organic layer is dried over sodium sulfate, concentrated and the residue is triturated with diethyl ether to give 6.1 g of the title compound. Physical characteristics are as follows:

Melting point 86°-87° C.

EXAMPLE 11

3-Benzyloxycarbonyl-4-(1H)-pyridone-6-carboxylic acid

A mixture of 4-oxymethoxymethyl-6-methyl-3-carboxylic acid pyridine benzyl ester (8.3 g) and selenium dioxide (120 ml) is heated at reflux for 2 hours. The hot reaction mixture is filtered and the solid is washed with dioxane (40 ml). Upon cooling the filtrate solution to room temperature, the title compound precipitates to give 3.0 g. The filtrate solution is concentrated and DMF (50 ml) is added to the residue. This solution is heated briefly and filtered. The remaining solution is concentrated and ethyl acetate (100 ml) is added to the residue. Upon standing at room temperature more solid precipitates which is filtered and dried to obtain an additional 3.8 g of the title compound. Physical characteristics are as follows:

Melting point 201°-204° dec.

EXAMPLE 12

3-Benzyloxycarbonyl-4-pyridon-6-yl-3-carbonylamino-2-imidazolidinone

3-Benzyloxycarbonyl-4-(1H)-pyridone-6-carboxylic acid (400 mg), aminoimidazolidinone (148 mg), DMAP (50 mg), HOBT (200 mg) and DCC (333 mg) are mixed in DMF (25 ml) at room temperature. After 16 hours the precipitated solid is filtered and the filtrate solution is concentrated under reduced pressure. The residue is washed with H$_2$O/CHCl$_3$. After concentrating, the organic layer is passed through a column of silica gel eluting with 4% methanol/chloroform to obtain 320 mg of the title compound. Physical characteristics are as follows:

Melting point 168°-170°.

EXAMPLE 13

(3-Carboxy-4-pyridon-6-yl)-3-carbonylamino-2-imidazolidinone

To a solution of 3-benzyloxycarbonyl-4-pyridon-6-yl-3-carbonylamino-2-imidazolidinone (800 mg) in DMF (30 ml) is added Pd-black (200 mg) under one atmosphere of H$_2$ gas. After one hour a small amount of toluene (5 ml) is added to the mixture and stirred for 10 minutes. The solid is filtered and the filtrate solution is concentrated. The residue is triturated with ethyl acetate to obtain 500 mg of the title compound. Physical characteristics are as follows:

Melting point 291°-294° dec.

EXAMPLE 14

Compound 14, (3S)-3-[2-(2-Amino-4-thiazolyl)-Z-(2)-carboxyisopropyloxyimino)acetamido]-1-[(3-carboxy-4-pyridon-6-yl)-carbonylamino-1-(2-imidazolidone-3-yl)sulfonylaminocarbonyl]-2-azetidinone trisodium salt Chlorosulfonylisocyanate (55 µl) is added to a heterogeneous mixture of (3S)-3-[2-(2-t-butoxycarbonylamino]-4-thiazolyl)-Z-(2-t-butoxycarbonylisopropyloxyimino)acetamido]azetidin-2-one (250 mg) in freshly distilled methylene chloride (5 ml) at −40° C. The mixture is slowly warmed to about −10° C. over 30 minutes and stirred for one hour. A mixture of (3-carboxy-4-pyridon-6-yl)-3-carbonylamino-2-imidazolidinone (135 mg) and N-methyl-N-(trimethylsilyl)trifluoroacetamide (0.35 ml) in anhydrous THF (4 ml) is stirred at room temperature for one and one-half hours, then the CSI adduct is added at 0° C. After 3 hours the mixture is concentrated and methylene chloride (4 ml) and cold trifluoroacetic acid (4 ml) are added. The mixture is warmed to room temperature and after one and one-half hours the mixture is concentrated and the residue is dissolved in water (60 ml) by adjusting pH of the solution to about 5.5 with aqueous sodium bicarbonate. After lyophilizing the aqueous solution, the product is purified by column chromatography on XAD-16 resin eluting with water followed by 6% acetonitrile/water to give the title compound. Physical characteristics are as follows:

IR (neat) 3180 (broad), 1770, 1726 cm$^{-1}$.

EXAMPLE 15

(3-Benzyloxyaminocarbonyl-4-pyridon-6-yl)-3-carbonylamino-2-imidazolidinone

A slurry of (3-carboxy-4-pyridon-6-yl)-3-carboxylamino-2-imidazolidinone (1 g) in DMF (40 ml) is heated at 70° C. to dissolve and then cooled to about 30° C. Carbonyldiimidazole (670 mg) is added and the mixture is allowed to warm to ambient temperature over 2.5 hours. Benzylhydroxyamine (550 mg) is added to the mixture at room temperature and stirred for 2 hours. The solvent is removed and the residue is shaken with methylene chloride (100 ml)/2N HCl (30 ml), filtered and dried to obtain 560 mg of the title compound. Physical characteristics are as follows:
Melting point 250°-253°.

EXAMPLE 16

(3-Hydroxyaminocarbonyl-4-pyrridone-6-yl)-3-carbonylamino-2-imidazolidinone (3-Benzyloxyaminocarbonyl-4-pyridon-6-yl)-3-carbonylamino-2-imidazolidinone (550 mg) is mixed in DMF with Pd-black (150 mg) under one atmosphere of $H_2$ gas. The mixture is filtered and the filtrate solution is concentrated under reduced pressure. Trituration of the residue with methanol produces the title compound. Physical characteristics are as follows:
Melting point 266°-269°.

EXAMPLE 17

Compound 17,
(3S)-3-[2-(2-Amino-4-thiazolyl)-Z-(2)-(carboxyisopropyloxyamino)acetamido]-1-[(3-hydroxyaminocarbonyl-4-pyridon-6-yl)carbonylamino-1-(2-imidazolidone-3-yl)sulfonylaminocarbonyl]-2-azetidinone To a slurry of (3S)-3-[2-(2-t-butoxycarbonylamino]-4-thiazolyl)-Z-(2-t-butoxycarbonylisopropyloxyimino)acetamido]azetidin-2-one (350 mg) in methylene chloride (5 ml) at −40° C. is added chlorosulfonylisocyanate (77 μl). The mixture is slowly warmed to 0° C. over 2 hours. A mixture of (3-hydroxyaminocarbonyl-4-pyridon-6-yl)-3-carbonylamino-2-imidazolidinone (190 mg) and N-methyl-N-(trimethylsilyl)trifluoroacetamide (0.5 ml) in THF (4 ml) is stirred for 2 hours at room temperature.

This silylated compound is added to the CSI adduct at 0° C. and the mixture is stirred for one hour. The mixture is concentrated under reduced pressure and the residue is dissolved in water by adjusting pH of the solution to about 6.1 with an aqueous sodium bicarbonate. After lyophilizing, the crude product is partially purified by XAD-16 column chromatography. The crude product is acidified by adding methylene chloride (15 ml) and trifluoroacetic acid (2 ml) and purified by means of HP-20 column chromatography eluting with $H_2O$ followed by 3% acetonitrile/water and then 6% acetonitrile/water to obtain 70 mg of the title compound. Physical characteristics are as follows:
IR (neat) 3200 (broad), 1782, 1723, 1666 cm$^{-1}$.

Following the procedures outlined in Example 17 but using 3-aminocarbonyl-4-pyridone-6-yl)-3-carbonylamino-2-imidazolidinone gives Compound 18:
(3S)-3-[2-(2-amino-4-thiazolyl)-2-(2)-(carboxyisopropyloxyamino)acetamido]-1-[(3-aminocarbonyl-4-pyridon-6-yl)carbonyl(amino-1-(2-imidazolidone-3-yl)sulfonylaminocarbonyl]-2-azetidinone. Physical characteristics are as follows:
M/C (μg/ml) (pseudomonas aeruginosa Culture No. 231) 8.

FORMULAS

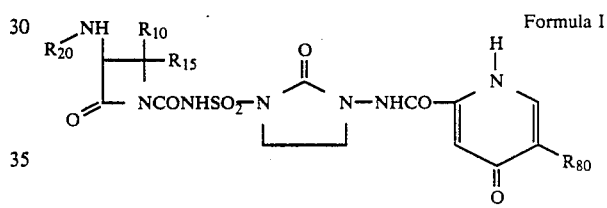

Formula I

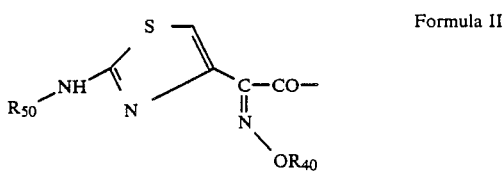

Formula II

STRUCTURE CHART

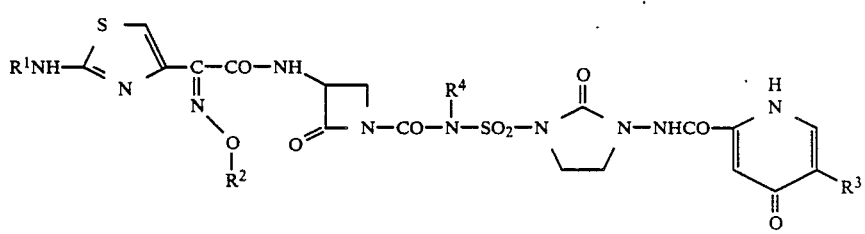

| Compound No. | $R^1$ | $R^2$ | $R^3$ | $R^4$ |
|---|---|---|---|---|
| 17 | H | $C(CH_3)_2CO_2H$ | CONHOH | H |
| 14 | H | $C(CH_3)_2CO_2Na$ | $CO_2Na$ | Na |
| 18 | H | $C(CH_3)_2CO_2$ | $CONH_2$ | H |

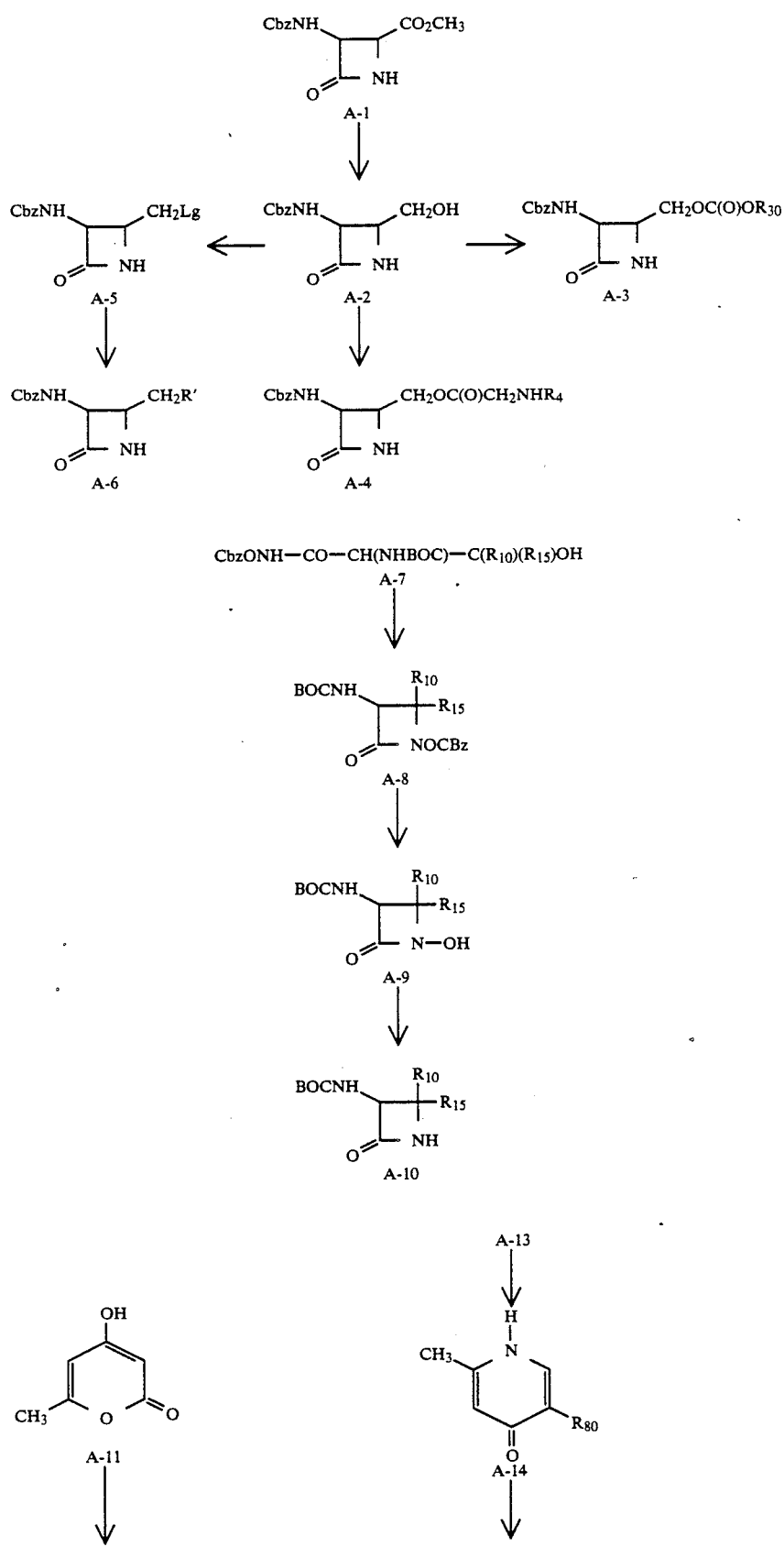

CHART A
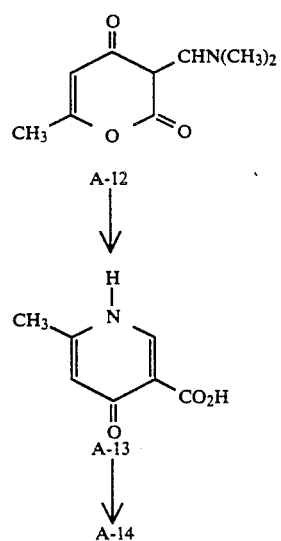
-continued
CHART A
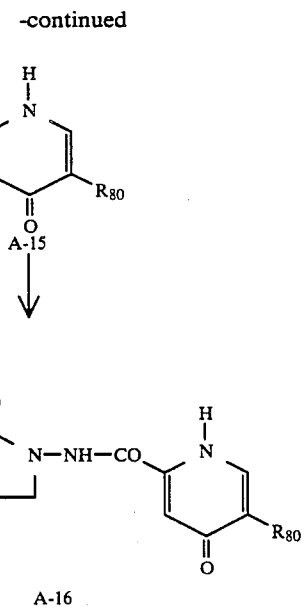
CHART B
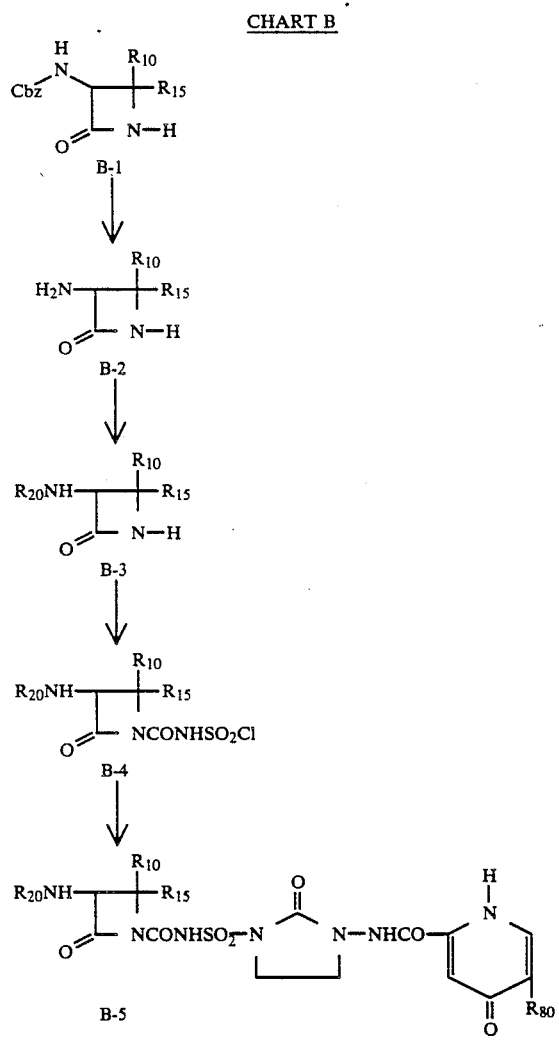
-continued
CHART B
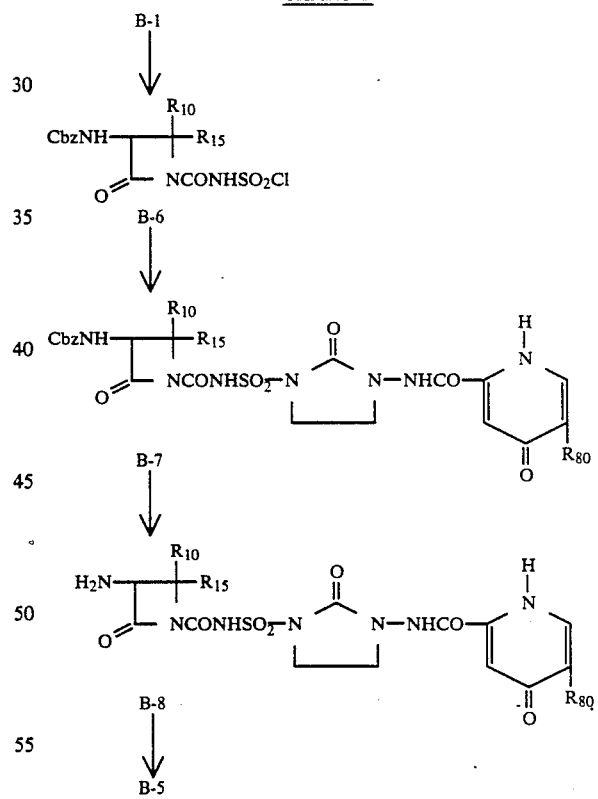
TABLE I
| | Minimum Inhibitory Concentration (μg/ml) | | |
|---|---|---|---|
| Organism | Culture Number | Compound 17 | Compound 14 |
| Staphylococcus aureus | 9218 | >128 | >128 |
| Staphylococcus aureus | 3665 | >128 | >128 |
| Staphylococcus aureus | 6685 | >128 | >128 |
| Streptococcus faecalis | 694 | >128 | >128 |
| Streptococcus pneumoniae | 41 | 64 | 64 |
| Streptococcus pyogenes | 152 | 4 | 4 |
| Citrobacter freundli | 3507 | 0.25 | 0.25 |

TABLE I-continued

| | | Minimum Inhibitory Concentration (μg/ml) | |
|---|---|---|---|
| Organism | Culture Number | Compound 17 | Compound 14 |
| Enterobacter cloacae | 9381 | 64 | 64 |
| Enterobacter cloacae | 9382 | 2 | 0.5 |
| Escherichia coli | 9379 | 0.5 | 0.25 |
| Escherichia coli | 9380 | 0.5 | 0.125 |
| Escherichia coli | 9451 | 0.25 | 0.125 |
| Klebsiella oxytoca | 9383 | 4 | 4 |
| Klebsiella oxytoca | 9384 | 0.5 | 0.25 |
| Klebsiella pneumoniae | 58 | 0.5 | 0.5 |
| Proteus vulgaris | 9679 | 0.125 | 0.06 |
| Serratia marcescens | 6888 | 2 | 0.5 |
| Pseudomonas aeruginosa | 231 | 4 | 0.5 |
| Pseudomonas aeruginosa | 9191 | 4 | 1 |

Compound 14 is (3S)-3-[2-(2-Amino-4-thiazolyl)-Z-(2)-carboxyisopropyloxyimino)acetamido]-1-[(3-carboxy-4-pyridon-6-yl)-carbonylamino-1-(2-imidazolidone-3-yl)sulfonylaminocarbonyl]-2-azetidinone trisodium salt Compound 17 is (3S)-3-[2-(2-Amino-4-thiazolyl)-Z-(2)-(carboxyisopropyloxyamino)acetamido]-1-[(3-hydroxyaminocarbonyl-4-pyridon-6-yl)carbonylamino-1-(2-imidazolidone-3-yl)sulfonylaminocarbonyl]-2-azetidinone

I claim:

1. A compound of Formula I and pharmacologically acceptable salts thereof;

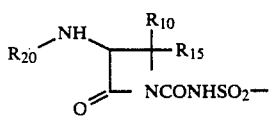

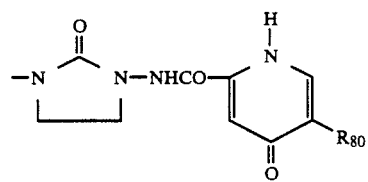

wherein $R_{10}$ and $R_{15}$ are the same or different and are
(a) hydrogen,
(b) $(C_1-C_8)$ alkyl,
(c) $(C_2-C_8)$ alkenyl,
(d) $(C_2-C_8)$ alkynyl,
(e) $(C_3-C_8)$ cycloalkyl,
(f) phenyl optionally substituted with between 1 and 3 substituents selected from the group consisting of halogen, nitro, $(C_1-C_4)$-alkyl, and $(C_1-C_4)$alkoxy,
(g) benzyl optionally substituted with between 1 and 3 substituents selected from the group consisting of halogen, nitro, $(C_1-C_4)$alkyl, and $(C_1-C_4)$alkoxy,
(h) $—CH_2OCOCH_2NHR_4$,
(i) $—CH_2OCO_2R_{30}$,
(j) $—CH_2F$, or
(k) $—CHF_2$;
wherein $R_4$ is
(a) hydrogen,
(b) $—COH$, or
(c) $—CO—O—C(CH_3)_3$;
wherein $R_{30}$ is $(C_1-C_8)$alkyl, $—(CH_2)_2NH_2$, $—(CH_2)_2NH(CH_3)$, $—(CH_2)_2NH—CO—O—C(CH_3)_3$, $—(CH_2)_2N(CH_3)—CO—O—C(CH_3)_3$, $—(CH_2)_2OC(O)NH_2$, $—(CH_2)_2Cl$, $—(CH_2)_2OCH_3$ or $—(CH_2)_2NH-COH$;

wherein $R_{20}$ is an acyl group derived from a carboxylic acid;

wherein $R_{80}$ is $—CO_2R_5$ or $—CONR_6R_7$;
wherein $R_5$ is hydrogen or $(C_1-C_4)$alkyl; and
wherein $R_6$ and $R_7$ are the same or different and are hydrogen, $(C_1-C_4)$ alkyl, or $—OH$ with the proviso that when $R_6$ is OH, $R_7$ is other than $—OH$.

2. A compound of claim 1 wherein $R_{20}$ is a oximinoacyl moiety of Formula II;

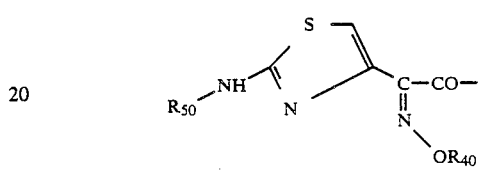

wherein $R_{40}$ is
(a) $—CH_3$,
(b) $—CH_2CO_2R_{41}$, or
(c) $—C(CH_3)_2CO_2R_{41}$,
wherein $R_{41}$ is
(a) hydrogen,
(b) $(C_1-C_4)$ alkyl,
(c) $—CH(C_6H_5)_2$,
(d) $—CH_2(C_6H_5)$, or
(e) a cation;
wherein $R_{50}$ is
(a) hydrogen,
(b) $—CO—O—C(CH_3)_3$,
(c) $—CO—O—CH_2—(C_6H_5)$, or
(d) $—C(C_6H_5)_3$.

3. A compound of claim 2; wherein $R_{10}$ and $R_{15}$ are hydrogen, wherein $R_{41}$ is hydrogen or a cation, and wherein $R_{50}$ is hydrogen.

4. A compound of claim 3; wherein $R_{80}$ is $CO_2H$, $CONHOH$ or $CONH_2$.

5. A compound of claim 4; (3S)-3-[2-(2-Amino-4-thiazolyl)-Z-(2)-carboxyisopropyloxyimino)acetamido]-1-[(3-carboxy-4-pyridon-6-yl)-carbonylamino-1-(2-imidazolidone-3-yl)sulfonylaminocarbonyl]-2-azetidinone trisodium salt, (3S)-3-[2-(2-Amino-4-thiazolyl)-Z-(2)-(carboxyisopropyloxyamino)acetamido]-1-[(3-hydroxyaminocarbonyl-4-pyridon-6-yl)carbonylamino-1-(2-imidazolidone-3-yl)sulfonylaminocarbonyl]-2-azetidinone, or (3S)-3-[2-(2-Amino-4-thiazolyl)-Z-(2)-(carboxyisopropyloxyamino)acetamido]-1-[(3-aminocarbonyl-4-pyridon-6-yl)carbonylamino-1-(2-imidazolidone-3-yl)sulfonylaminocarbonyl]-2-azetidinone.

* * * * *